United States Patent
Johnson (10) Patent No.: US 9,093,187 B1
(45) Date of Patent: Jul. 28, 2015

(54) FIXED GANTRY CT SYSTEM HAVING A NON-UNIFORM SLIT

(71) Applicant: SureScan Corporation, Endicott, NY (US)

(72) Inventor: Eric Johnson, Greene, NY (US)

(73) Assignee: SureScan Corporation, Endicott, NY (US)

( * ) Notice: Subject to any disclaimer, the term of this patent is extended or adjusted under 35 U.S.C. 154(b) by 70 days.

(21) Appl. No.: 14/083,757

(22) Filed: Nov. 19, 2013

(51) Int. Cl.
| | |
|---|---|
| *A61B 6/03* | (2006.01) |
| *G21K 1/02* | (2006.01) |
| *G21K 7/00* | (2006.01) |
| *G21K 1/04* | (2006.01) |
| *G01N 23/04* | (2006.01) |

(52) U.S. Cl.
CPC ............ *G21K 1/04* (2013.01); *G01N 23/046* (2013.01)

(58) Field of Classification Search
CPC .......... G01N 2223/076; G01N 23/223; A61B 6/485; A61B 6/4021; A61B 6/4291
USPC .......... 378/4, 9, 21, 46, 62, 87, 147, 149, 119
See application file for complete search history.

(56) References Cited

U.S. PATENT DOCUMENTS

| | | | |
|---|---|---|---|
| 6,243,438 B1 * | 6/2001 | Nahaliel et al. | 378/19 |
| 7,280,631 B2 | 10/2007 | DeMan et al. | |
| 7,593,502 B2 | 9/2009 | Katcha et al. | |
| 8,983,024 B2 * | 3/2015 | Zhang et al. | 378/4 |
| 2004/0264626 A1 * | 12/2004 | Besson | 378/4 |
| 2011/0211666 A1 * | 9/2011 | Ying et al. | 378/9 |

* cited by examiner

*Primary Examiner* — Nikita Wells
(74) *Attorney, Agent, or Firm* — Mark Levy; Hinman, Howard & Kattell, LLP (57) ABSTRACT

A volumetric stationary CT system has at least one stationary array of x-ray detectors extending proximate at least a portion of an imaging volume, at least one stationary x-ray source proximate the stationary array or arrays of x-ray detectors, and a collimator having a slit with a non-uniform opening width. The collimator is intermediate the stationary x-ray source and the stationary array of x-ray detectors. The result is a uniform flux normal to the detector array across the entire length thereof.

9 Claims, 11 Drawing Sheets

FIXED GANTRY CT SYSTEM HAVING A NON-UNIFORM SLIT

FIELD OF THE INVENTION

The present invention relates to computed or computer tomography (CT) systems and, more particularly, to a stationary or fixed gantry CT system capable of generating a uniform flux normal to the detector array across the entire length thereof.

BACKGROUND OF THE INVENTION

Rotating gantry CT systems have been the standard since the first systems were developed in the 1970s. While systems using this geometry are computationally efficient, they have several drawbacks, among them the mechanical complexity of the rotating components.

U.S. Pat. No. 7,593,502, issued to Katcha, et al. and assigned to General Electric Company on Sep. 22, 2009 for METHODS AND APPARATUS FOR FAST ROTATION SPEED SCANNERS is but one example of a rotating gantry CT system that includes a gantry having a stationary member coupled to a rotating member. The rotating member has an opened area proximate an axis about which the rotating member rotates. An x-ray source is provided on the rotating member. An x-ray detector may be disposed on the rotating member and configured to receive x-rays from the x-ray source.

In some ways, stationary or fixed gantry systems represent an improvement over rotating gantry systems, as the fixed gantry systems eliminate the need to rotate the massive x-ray sources and detector arrays and can make more efficient use of space by using a rectangular aperture. There are, however, concomitant disadvantages to fixed gantry systems. One of these is the variation in the flux normal to the detectors' surface due to variations in the distance to, and angle with, the source spot. In a typical fixed-gantry CT system, such as depicted in U.S. Pat. No. 7,280,631, issued to De Man, et al. and also assigned to General Electric Company on Oct. 9, 2007 for STATIONARY COMPUTED TOMOGRAPHY SYSTEM AND METHOD, the surface-normal flux can vary by as much as 3:1 across a one meter detector array. It is obvious that the signal-to-noise ratio of such a system could be improved by using a source that produced a more uniform flux normal to the detector array across its entire length. This can be achieved by the use of a collimator having a slit of non-uniform width.

Additional benefits can be realized in the slit design if a defocused source-spot is used. A larger spot produces a fan-beam more uniform across its central plane and allows the peak value to be varied through a greater range. This makes angular alignment across large distances less critical.

The use of a non-uniform slit in fixed gantry CT systems can therefore improve the signal-to-noise ratio and ease requirements for alignment of the x-ray source.

SUMMARY OF THE INVENTION

In accordance with the present invention, there is provided a volumetric stationary CT system having at least one stationary array of x-ray detectors extending proximate at least a portion of an imaging volume, a stationary x-ray source proximate the stationary array or arrays of x-ray detectors, and a collimator having a slit with a non-uniform opening width. The collimator is intermediate the stationary x-ray source and the stationary array of x-ray detectors. The result is a uniform flux normal to the detector array across the entire length thereof.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

The present invention is a volumetric stationary CT system having at least one stationary array of x-ray detectors extending proximate at least a portion of an imaging volume, a stationary x-ray source proximate the stationary array or arrays of x-ray detectors, and a collimator having a slit with a non-uniform opening width. The collimator is intermediate the stationary x-ray source and the stationary array of x-ray detectors.

In describing the invention it is important to understand the terminology used herein.

Radiance, L, is used to describe the quantity of radiation, within a solid angle, passing through a plane with its normal at an angle θ (radians) from the source. The expression for radiance is:

$$L = d^2\Phi_0/d\Omega dA \cos\theta \quad [1]$$

where $\phi_0$ is the total radiated flux (W), $\Omega$ is the subtended solid angle (sr), θ is the angle between the direction of propagation and the surface normal, and A is the area of the surface ($m^2$).

A refers to an area on either the source or the detector, depending on whether the emitted radiance or the received radiance is to be calculated.

Radiant flux density, or irradiance, is the power incident on a surface, with units of $W/m^2$.

Figure 1:
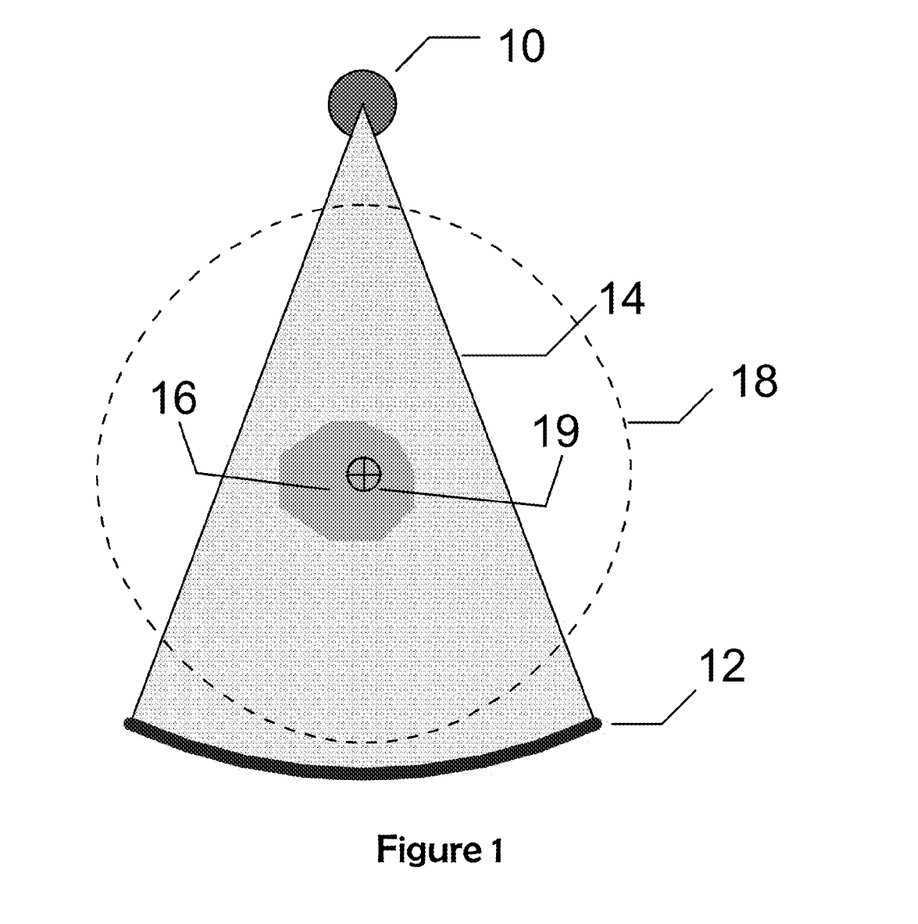
FIG. 1 is an axial view of a standard rotating gantry configuration of a CT scanner.

Referring now to FIG. 1, there is shown the geometry of a rotating gantry CT system, as commonly practiced. In this arrangement, a fan-beam 14 emanates from an x-ray source-tube 10 and illuminates an array of x-ray detectors 12. The source 10 and detector array 12, along with electronics, a thermal control system and other associated equipment (not shown) are rotated about a central axis 19 that lies in, or near, the object to be analyzed, 16. Aperture 18 is shown by the phantom line in the Figure.

The x-ray detector array 12 may be composed of scintillating detectors or by direct conversion detectors such as semi-conductor CdZnTe crystals. While the former are substantially linear, with a wide dynamic range, semi-conductor-based detectors are non-linear and operate best over a limited range of irradiance. Individual x-ray detectors in array 12 of a rotating gantry system are placed at a uniform radial distance from the source 10 in order to eliminate the variation in flux at each detector's surface from the $1/r^2$ spatial diminution. This arrangement also ensures that the surface of each x-ray detector is normal to the direction of wave propagation.

Figure 2:
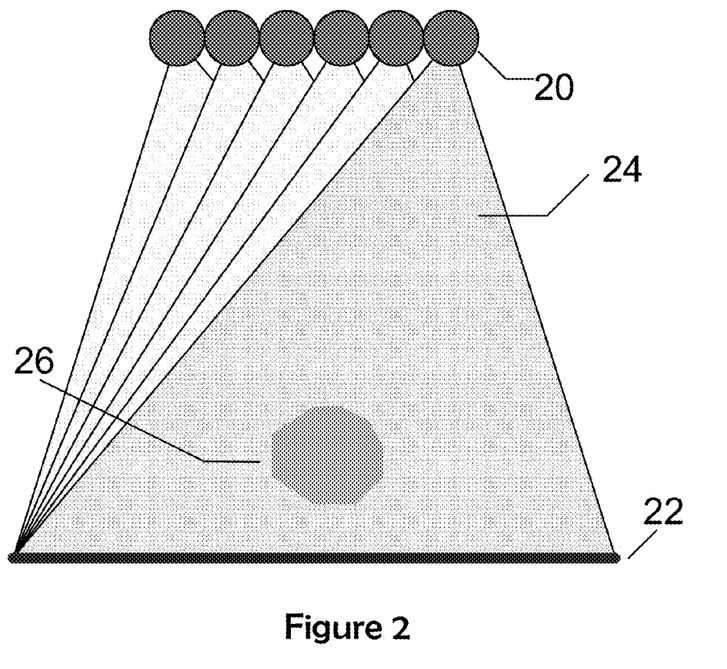
FIG. 2 is an axial view of a fixed-gantry system showing one scan plane.

Referring to FIG. 2, in which the angle $\theta=\pi/4$, for a fixed gantry system there is shown a great difference in the distance between x-ray source 20 and detector array 22, and in the incidence angle of the photons. This is particularly true for sources and detectors at the extremities of detector arrays 22, as shown in the Figure. Multiple scan planes with different orientations are typically used. The distance between source tube 20 and various points along detector array 22 varies by a ratio of 1.4:1. The radiance therefore varies by 2:1 and, when the angle of incidence is taken into account, the flux density varies by 2.8:1. Clearly, it would be advantageous to reduce this variation so that the signal-to-noise ratio can be maximized and non-linearities that occur in solid-state detectors can be avoided.

Figure 3:
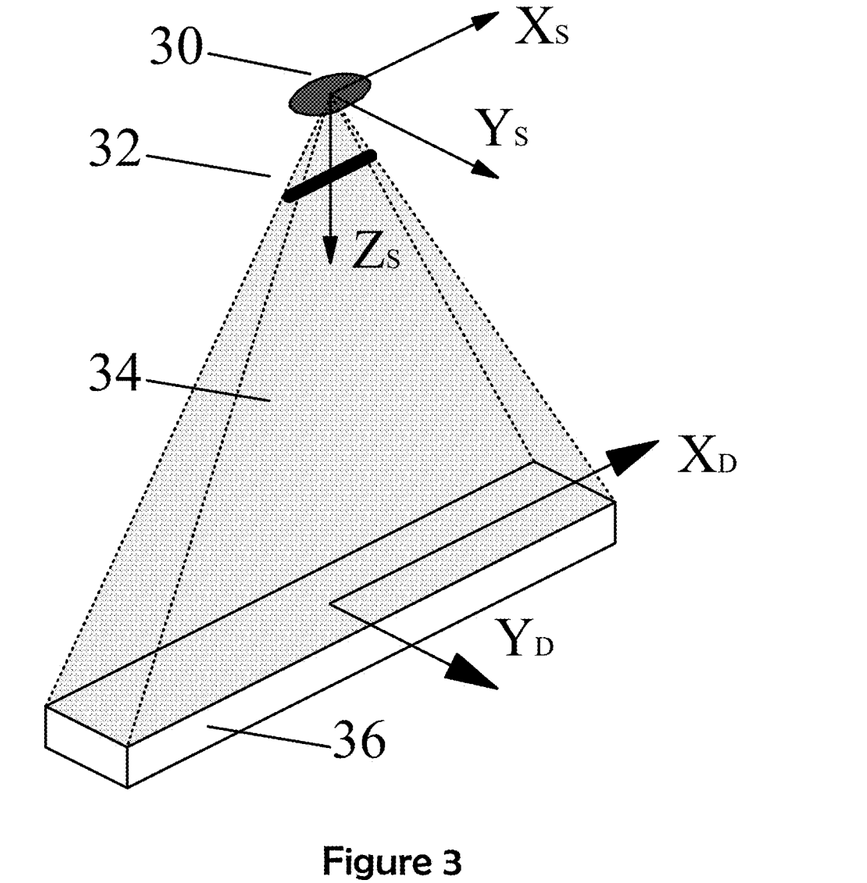
FIG. 3 shows the coordinate system used to describe the invention.

Referring now to FIG. 3, the geometry depicted helps describe the variable-width collimator slit 32. X-rays originate from a small spot 30 where electrons interact with a target, typically tungsten, within a vacuum tube (not shown). X-rays radiate in all directions. However, the target and additional shielding (not shown) block nearly all radiation except that passing through the collimator slit 32. Collimator slit 32 is most commonly formed by an opening in a high-density material such as lead, tungsten or tantalum.

A fan-beam 34 is defined by the dimensions of slit 32 and propagates in direction $Z_S$. In this case the subscript s indicates the Cartesian coordinate system whose origin is at the focal spot 30.

A second coordinate system, indicated by the subscript D, is centered on the surface of detector array 36 that is nearest focal spot 30. Its origin lies on the $Z_S$ axis. The $X_D$ and $Y_D$ axes are parallel to corresponding axes $X_S$ and $Y_S$.

Figure 4:
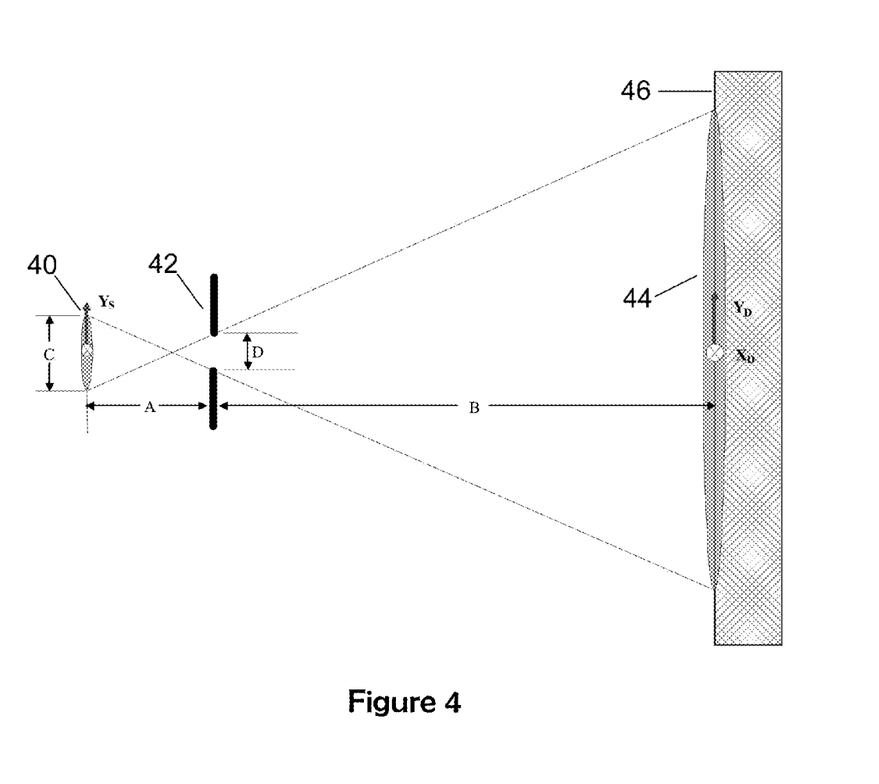
FIG. 4 shows a 2-dimensional section across the fan-beam with exemplary dimensions.

FIG. 4 is a two-dimensional view, taken in the $Y_S$-$Z_S$ plane of FIG. 3. Focal spot 40 is defined by dimension C at its widest point along the $Y_S$ axis. The distance from focal spot 40 to collimator slit 42 is defined by dimension A. The distance between collimator slit 42 and the nearest surface of x-ray detector array 46 is dimension B. It should be noted that the long dimension of slit 42 and of the detector array 46 is normal to the cross-section shown in the Figure.

Focal spot 40 produces an x-ray fan 44 on the surface of detector array 46 whose width and intensity are dependent on dimensions A, B, C and D. The irradiance across fan 44, in direction $Y_D$, is a function of these same dimensions and of the radiance at various points within focal spot 40. The calculation of the fan profile is described hereinbelow for a simple radiance distribution amenable to closed-form solution. Numerical methods can also be used to calculate the fan profile, using a more realistic distribution from electro-dynamic modeling or from measurements.

Figure 5:
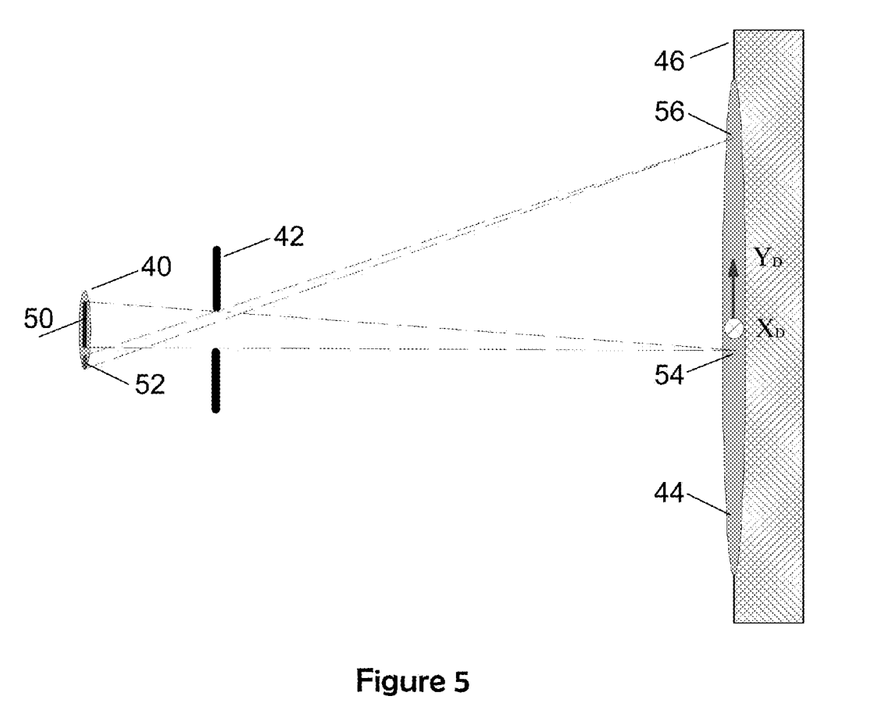
FIG. 5 shows the integration limits superimposed on the 2-dimensional section of the beam.

Reference is made to FIGS. 4 and 5 in the following description. Like numbers are used to describe like features in the two Figures.

Focal spot 40 is idealized as a circular source with diameter C and a uniform, hemispherical radiance. At any point along the surface of the x-ray detector array 46, the portion of focal spot 40 that contributes to the irradiance is determined by the opening of slit 42 in the $Y_S$ direction. It is assumed that slit 42 is sufficiently long in the $X_S$ direction to illuminate x-ray detector array 46 along its entire length. Given this assumption, focal spot 40 can be treated as a one-dimensional source with a radiated flux per unit length of $\phi(Y_S)dY_S$.

For a uniform, circular source, $\phi(Y_S)dY_S$ is:

$$\Phi(Y_s)dY_s = \frac{2}{\pi R^2}\Phi_0\sqrt{R^2 - Y_S^2}\, dY_S, \text{ with } R = C/2 \quad [2]$$

If collimator slit 42 is sufficiently narrow, as shown in FIGS. 4 and 5, then the flux radiated by the source is limited in the $Y_S$ direction. At point 54 near the center of detector array 46, most of the focal spot, region 50, contributes to the irradiance. Another point 56 farther from the center of detector array 46 is irradiated by only a small portion 52 of focal spot 50. In both cases, flux radiating from some portion of focal spot 50 is blocked by the slit 42.

To determine the irradiance at any point $X_D$, $Y_D$ on the surface of x-ray detector array 46, the function $\phi(Y_S)dS$ is integrated using the limits determined by the half-width R of slit 42 and dimensions A and B. The integration limits are:

$$M_1, M_2 = \pm R\left(1 + \frac{A}{B}\right) - \frac{A}{B}Y_D \quad [3]$$

These limits do not change with $X_D$ since the ratio NB remains constant at all points along the detector array 46. Integrating eq. [2] and applying the limits from eq. [3], the total radiated flux passing through the slit 42, on the ray-path through any point $X_D$, $Y_D$ is:

$$\frac{\Phi_0}{\pi R^2}\int_{M2}^{M1} 2\sqrt{R^2 - Y_S^2}\, dY_S = \frac{\Phi_0}{\pi R^2}\left[Y_S\sqrt{R^2-Y_S^2} + R^2\sin^{-1}\frac{Y_S}{|R|}\right]_{M2}^{M1} \quad [4]$$

and the irradiance on an incremental area of detector array 46 is approximately:

$$L \approx \frac{\Phi_0}{\pi R^2}\left[\frac{Z_S^2}{\Delta X_D \Delta Y_D \cos^3\vartheta}\right]\left[Y_S\sqrt{R^2-Y_S^2} + R^2\sin^{-1}\frac{Y_S}{|R|}\right]_{M2}^{M1} \quad [5]$$

where $\theta$ defines the angle from the center of the source 30 to the evaluation point $X_D$, $Y_D$ on detector 36 (FIG. 3). Numerical methods can be used to evaluate eq. [5].

Figure 6:
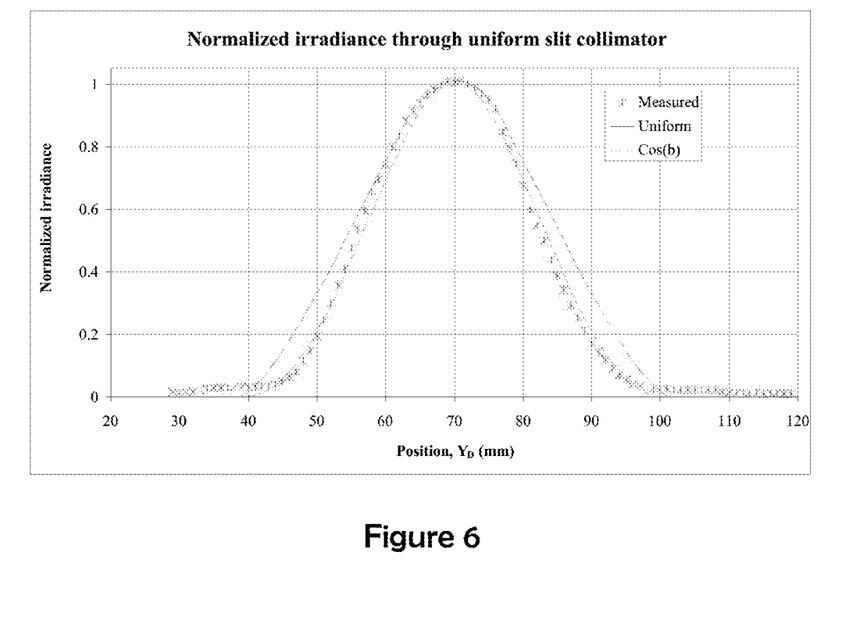
FIG. 6 compares the beam profile calculated using the method of the invention to a measured profile.

Referring now to FIG. 6, the measured irradiance from a straight collimator slit is compared to values calculated using the methods described above. Irradiance was measured using a commercially available x-ray tube and a pixilated CdZnTe detector array with a 1 mm pitch. Measurements were made on the $Y_d$ axis where $X_D=0$. After correcting for pixel sensitivity, the irradiance was normalized and plotted as discrete points in the Figure. The geometry of the test system was used in all subsequent calculations.

Assume first a uniform radiant flux $\phi$ (eq. [5]) was used to calculate the profile shown by the solid, upper line. After normalization the profile can be seen to match the experimental data well near the center portion of the fan. At points far from the center, the model overestimates the irradiance.

Referring to FIG. 5, the irradiance at point 56 is a function of the radiance of a small portion 52 near the periphery of source spot 40. This suggests that $\phi$ would be better described by a function that decreases at the periphery.

Once again referring to FIG. 6, the beam profile was plotted using a cosine function to describe $\phi$. After normalization the dashed, green line shows an excellent fit to the outer portion of the beam. More sophisticated models of $\phi$ can be used to obtain a nearly exact fit to the experimental data.

Figure 7:
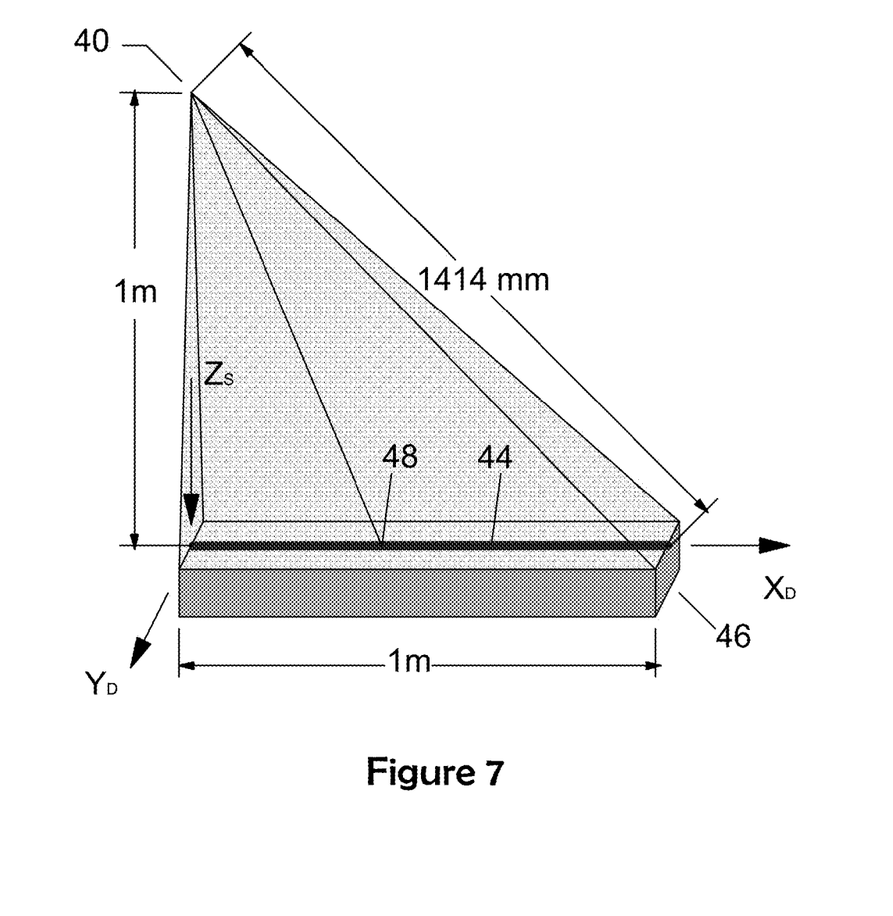
FIG. 7 shows the dimensions of an exemplary embodiment of the invention.

With reference to FIGS. 5 and 7, an exemplary embodiment of the invention is herein described. Dimensions A and B have been arbitrarily chosen to be 0.1 and 1.0 meter respectively. A source-spot 40 with a 2 mm diameter, C, is typical of commercial x-ray tubes and is used in this embodiment. The width D of slit 42 is calculated so that a detector array 46 1.0 meter long has nearly uniform irradiance along its length. The exemplary embodiment is shown with focal spot 40 directly above the end of detector array 46, illuminating pixels 44 along the $X_D$ axis. The angle between the source and the extremities of detector array 46 is 45°. Source 40 and collimator slit 42 have been rotated about axis $Y_S$ so that the fan illuminates the entire length of detector array 46 and the raypath normal to the collimator intersects detector array 46 at point 48, where $X_D$=414 mm. At a point $X_D$=0, $Z_S$=1 the values of A and B are 108 mm and 892 mm, respectively, with an angle of incidence, e, of 0°. At a point 1 m along the $X_D$ axis, these values are 108 mm, 1306 mm and 45° respectively. Using eq. [1], it can be shown that the radiance at the source, in the direction of detector 46 at XD=1, is about 2.8 times that at XD=0 to provide the same irradiance. This is due to the $1/\Omega A \cos \theta$ term that appears in eq. [1].

Figure 8:
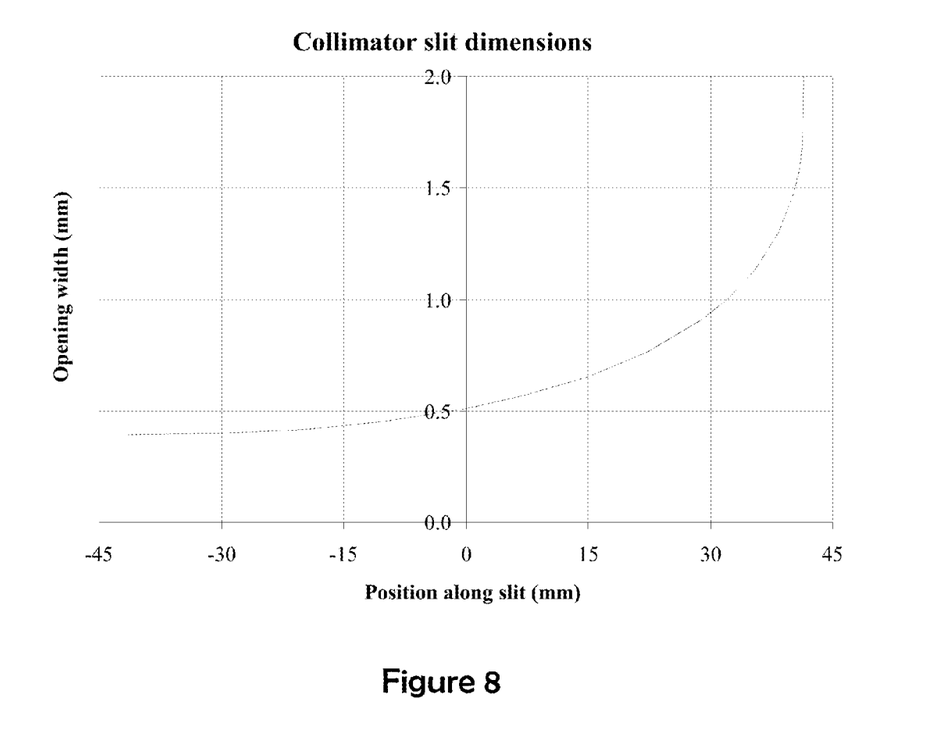
FIG. 8 is a graph of the ideal collimator profile for the exemplary embodiment.

Numerical methods, which are easily implemented by those skilled in the art, have been used to evaluate eqs. [3] and [5] to find the values of D that produce a uniform irradiance along the pixel array 44 of detector 46. The ideal collimator profile for this exemplary embodiment is shown in FIG. 8.

Figure 9:
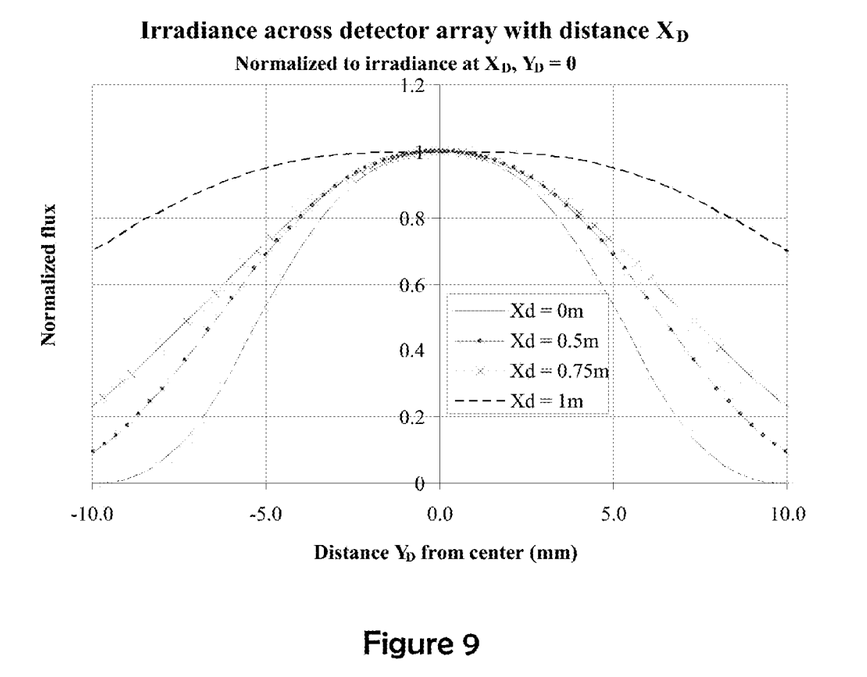
FIG. 9 is a graph showing the irradiance across the detector array for the exemplary embodiment.

Referring now to FIG. 9, while the irradiance along the centerline of pixel array 44 is uniform ($Y_D$=0), it varies in $Y_D$ from one end of the array to the other ($X_D$=0 to 1) for four points along detector array. In typical CT applications, the width of pixel array 44 is 1 mm to 4 mm. Over this range, the irradiance at $X_D$=0 varies by <10%.

It should be noted that the widest part of the fan, at $X_D$=1, is at the farthest point from the source. This eases the requirements for angular alignment of the source and collimator at the point where any errors are magnified by the extreme distance.

Figure 10:
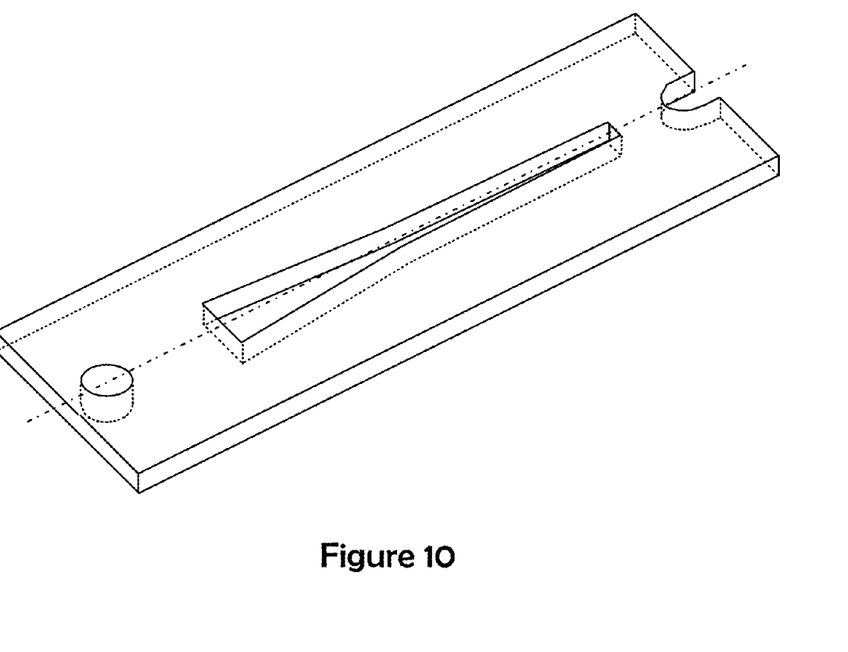
FIG. 10 is an illustration of a second exemplary embodiment of the profiled collimator.

Once the collimator profile has been calculated it can be programmed on a computer-controlled milling machine and precisely cut. It is, however, possible to achieve an approximately uniform irradiance using bi-linear or multi-linear profiles that can be cut on much less sophisticated equipment. An illustration of a bi-linear collimator slit is shown in FIG. 10.

Figure 11:
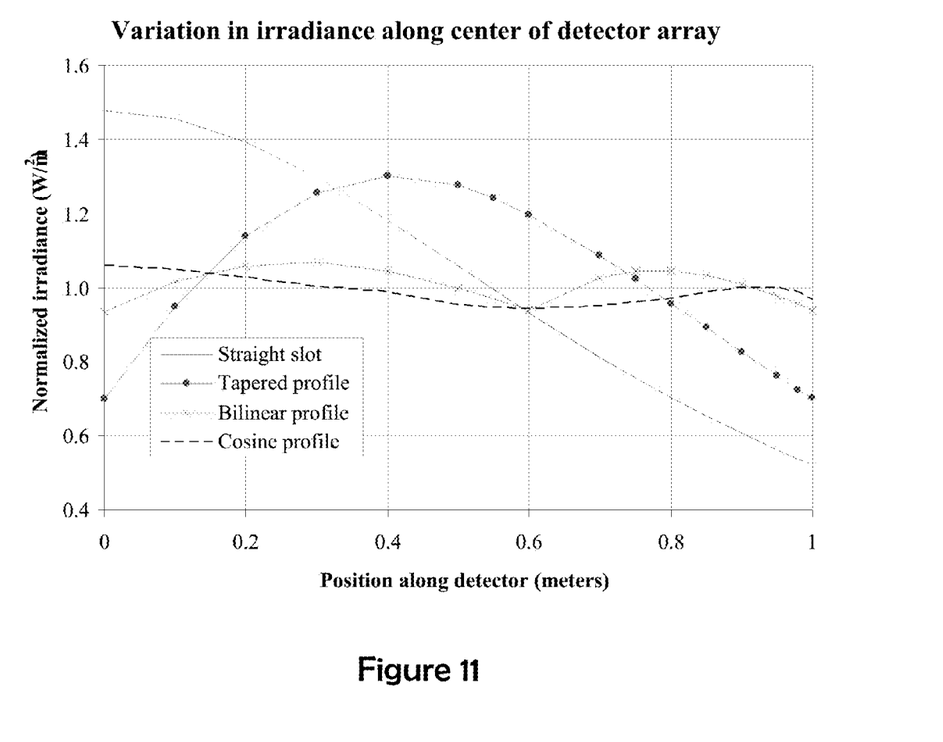
FIG. 11 shows the irradiance along the centerline of a detector array for several collimator profiles.

The irradiance along the centerline of pixel array 44 has been calculated for several profiles and plotted in FIG. 11. Table 1 shows the variation in irradiance along the center of the array 44 for these exemplary collimator profiles. This variation is calculated as $[(L_{max}-L_{min})/(2L_{avg})]$. A simple bi-linear profile reduces the variation along array 44 to within ±7%.

Table 1

Maximum Variation of Irradiance Along Array Centerline

| Collimator profile | Variation |
| --- | --- |
| Straight | ±48% |
| Tapered | ±26% |
| Bi-linear | ±7% |
| Cosine | ±6% |
| Optimum | ≈0 |

Due to the aforementioned variation of <10% across the detector array 44 at $X_D$=0, an additional benefit is derived by using a profile that provides a slightly increased irradiance at this point. The advantage, however, is small.

It is apparent that there are many possible collimator profiles resulting in a more uniform irradiance of the detector array. As a result, the detectors, whether solid-state, direct conversion devices such as CdZnTe, or scintillators, can operate under their optimum conditions. Dynamic range and signal-to-noise can be maximized. These advantages are obvious to one well-versed in the art.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A volumetric stationary CT system comprising:
    a) at least one stationary array of x-ray detectors extending proximate at least a portion of an imaging volume;
    b) at least one stationary x-ray source proximate said at least one stationary array of x-ray detectors; and
    c) a collimator having a slit of a predetermined length with an adjustable opening width, said collimator disposed intermediate each of said at least one stationary x-ray source and said at least one stationary array of x-ray detectors; said slit for providing uniform irradiance at all points along said at least one stationary array of x-ray detectors.

2. The volumetric stationary CT system in accordance with claim 1, wherein said at least one stationary array of x-ray detectors comprises at least one of the group: scintillators and direct conversion x-ray detectors.

3. The volumetric stationary CT system in accordance with claim 1, wherein said irradiance varies by <10% over said at least one stationary array of x-ray detectors.

4. The volumetric stationary CT system in accordance with claim 1, further comprising a target disposed in said imaging volume and wherein said stationary x-ray source produces a defocused spot on said target.

5. The volumetric stationary CT system in accordance with claim 1, said at least one stationary x-ray source comprising an x-ray source tube having a focal spot, the dimensions of which focal spot being greater than said length of said collimator slit.

6. The volumetric stationary CT system in accordance with claim 4, wherein said defocused spot has a diameter greater than 1 mm, allowing a uniform irradiance across said at least one stationary array of x-ray detectors.

7. A method of calculating the profile of a non-uniform collimator slit in a volumetric stationary CT system comprising a stationary array of x-ray detectors extending proximate at least a portion of an imaging volume, a stationary x-ray source proximate said stationary array of x-ray detectors, said non-uniform collimator slit disposed intermediate said stationary x-ray source and said stationary array of x-ray detectors, the steps comprising:
   a) integrating the radiance of a source spot in one dimension;
   b) determining integration limits from the slit width along the projection of the ray path from a point on the centerline of said stationary array of x-ray detectors to said source spot; and
   c) adjusting the width of said slit to provide uniform irradiance at all points along said stationary array of x-ray detectors.

8. The method of calculating the profile of a non-uniform collimator slit in accordance with claim 7, wherein said integrating step (a) is determined by at least one of the group: closed-form and numerically.

9. The method of calculating the profile of a non-uniform collimator slit in accordance with claim 7, wherein said irradiance is calculated to be uniform to within ±10% over said stationary array of x-ray detectors.

* * * * *